United States Patent
Schlienger et al.

(10) Patent No.: US 9,205,185 B2
(45) Date of Patent: Dec. 8, 2015

(54) PUMP UNIT FOR EXPRESSING MILK

(71) Applicant: Medela Holding AG, Baar (CH)

(72) Inventors: Andre Schlienger, Maschwanden (CH); Etienne Furrer, Zug (CH); Mario Rigert, Buchrain (CH); Deanna Gilbert, Arlington Heights, IL (US)

(73) Assignee: Medela Holding AG, Baar (CH)

( * ) Notice: Subject to any disclaimer, the term of this patent is extended or adjusted under 35 U.S.C. 154(b) by 72 days.

(21) Appl. No.: 13/828,333

(22) Filed: Mar. 14, 2013

(65) Prior Publication Data

US 2014/0128806 A1     May 8, 2014

Related U.S. Application Data

(60) Provisional application No. 61/722,563, filed on Nov. 5, 2012.

(51) Int. Cl.
  *A61M 1/06*     (2006.01)

(52) U.S. Cl.
  CPC ........... *A61M 1/06* (2013.01); *A61M 2205/586* (2013.01)

(58) Field of Classification Search
  CPC ..... A61M 1/06; A61M 1/066; A61M 1/0072; A61J 7/0046; A61J 9/005; A61J 9/006; A61J 9/008; A61J 9/0607–9/0692; B65B 3/003
  USPC ...................... 604/72–74; 215/390, 208, 321; 232/41 R
  See application file for complete search history.

(56) References Cited

U.S. PATENT DOCUMENTS

| 4,680,028 | A |   | 7/1987  | Stuart |         |
|-----------|---|---|---------|--------|---------|
| 5,571,084 | A |   | 11/1996 | Palmer |         |
| D420,448  | S | * | 2/2000  | Brown et al. | ................ D24/197 |
| 6,073,788 | A |   | 6/2000  | Stroud |         |

(Continued)

FOREIGN PATENT DOCUMENTS

| EP | 1034807 A1    | 9/2000  |
| WO | 2008057218 A2 | 5/2008  |
| WO | 2008137678 A1 | 11/2008 |

OTHER PUBLICATIONS

International Search Report for PCT/EP2013/072827, Jan. 3, 2014.

*Primary Examiner* — Nicholas Lucchesi
*Assistant Examiner* — Melissa A Snyder
(74) *Attorney, Agent, or Firm* — McDonnell Boehnen Hulbert & Berghoff LLP

(57) ABSTRACT

A pumping unit for use in a device for expressing human breast milk comprises a breast shield for resting against a mother's breast and a dimensionally stable or approximately dimensionally stable milk collection container for receiving the expressed mother's milk. The breast shield comprises a first longitudinal center axis, and the milk collection container comprises a second longitudinal center axis, wherein the milk collection container is detachably attachable to the breast shield, and wherein in the attached state of the milk collection container the first longitudinal center axis is arranged at an angle to the second longitudinal center axis. In the attached state the milk collection container is movable relative to the breast shield, and consequently the angle between the first and second longitudinal center axes is variable. The pumping unit according to the invention can be designed in a compact and space-saving manner and is particularly suited to a hands-free arrangement.

15 Claims, 8 Drawing Sheets

(56) References Cited

U.S. PATENT DOCUMENTS

| | | | |
|---|---|---|---|
| 6,092,680 A | 7/2000 | Pillado | |
| 6,461,324 B1 * | 10/2002 | Schlensog | 604/74 |
| 7,223,255 B2 | 5/2007 | Myers et al. | |
| 8,591,458 B2 * | 11/2013 | Britto et al. | 604/74 |
| 2004/0087898 A1 | 5/2004 | Weniger | |
| 2008/0262420 A1 | 10/2008 | Dao et al. | |
| 2009/0171270 A1 | 7/2009 | Roehrig | |

* cited by examiner

PUMP UNIT FOR EXPRESSING MILK

CROSS-REFERENCE TO RELATED APPLICATIONS

This application claims the benefit of U.S. Provisional Application Ser. No. 61/722,563 filed No. 5, 2012, the contents of which are fully incorporated herein by reference.

TECHNICAL FIELD

The present invention relates to a pumping unit for use in a device for expressing human breast milk, to a breast shield, to a milk collection container, and to a coupling unit.

BACKGROUND

Devices for expressing human breast milk are well known. There are generally two types of such devices: the first type is manually operated, i.e. the negative pressure necessary for expressing is generated by manually operating the vacuum pump. In the second type the vacuum pump is operated by means of an electric motor.

In these devices, pumping units are used that comprise a breast shield and a milk collection container connected to the latter. Typically, the breast shield comprises a funnel which rests against the breast so as to form a seal. The container is removably connected to the breast shield, either directly or by way of a hose connection. If the container is designed so as to be dimensionally stable, in particular rigid, it can be used both as a storage container for the milk and as a bottom part of a milk bottle for administering the milk. Such dimensionally stable containers are easy to handle, in particular when they are of a self-standing design. In other embodiments such containers are designed as soft bags. Soft bags are associated with a disadvantage in their use in that prior to being closed to form a tight seal they have to be handled very carefully to prevent any outflow of milk. Furthermore, prior to being administered to a baby, the milk needs to be poured into some other container.

US 2004/0087898 and WO 2008/057218 disclose pumping units with a dimensionally stable milk collection container that is connected to the breast shield by way of a screw-type connection. The angle between the longitudinal centre axis of the breast shield and the longitudinal centre axis of the milk collection container exceeds 90°.

US 2008/0262420 discloses a breast shield with a milk collection chamber. This breast shield can be fastened in a brassiere. From the breast shield a flexible line leads to a milk collection container that is arranged in a belt.

U.S. Pat. No. 7,223,255 and WO 2008/137678 show breast shields with an integrated vacuum pump and a milk collection bag that is connected to the breast shield by way of a line.

SUMMARY

It is an object of the invention to create a pumping unit comprising a dimensionally stable or approximately dimensionally stable milk collection container that is designed so as to be as compact and space-saving as possible and that provides optimal comfort to the mother during pumping.

In one aspect, the pumping unit for use in a device for expressing human breast milk comprises a breast shield for resting against a mother's breast and a dimensionally stable or approximately dimensionally stable milk collection container for receiving the expressed milk. The breast shield comprises a first axis, in particular a longitudinal centre axis, and the milk collection container comprises a second axis, in particular a longitudinal centre axis. The milk collection container is detachably or removably attachable to the breast shield. Preferably, the breast shield is held by the milk collection container or vice versa. In the attached state of the milk collection container the first axis is arranged at an angle to the second axis. According to one embodiment of the invention, in the attached state the milk collection container is movable and/or pivotable relative to the breast shield, and consequently the angle between the first axis and the second axis is variable.

Since the angle between the milk collection container and the breast shield can be varied, and preferably be set as required, the angle can be adjusted according to the individual anatomical circumstances of the mother's breast. Prior to expressing and preferably also during expressing, the mother can set an angle that is optimal for her, and if the position changes, can at any time vary the angle as required.

Large breasts require an angle that differs from that of smaller breasts; the same applies to slim and corpulent women. Because of this adaptability the milk collection container can be arranged so as to be relatively close to the body and to the breast shield. Furthermore, it is not necessary to provide a long intermediate region between the breast shield and the container. The pumping unit can thus be designed so as to be compact and space-saving.

Thanks to the ability to vary the position of the container relative to the breast shield, the breast shield can even be worn underneath a brassiere, although a dimensionally stable or even rigid collection container is arranged in the direct vicinity of said breast shield. A so called hands-free operation, in which neither the collection container nor the breast shield need to be held manually, is thus possible.

In one example embodiment, the collection container is connected to the breast shield by means of a single interface. This interface is preferably used at the same time as a connection channel to lead the milk from the breast shield to the collection container.

In one aspect, a first coupling part and a second coupling part are provided, which together enable the relative movement, wherein the first coupling part is arranged on the breast shield and the second coupling part is arranged on the milk collection container. The milk collection container may comprise a container part and a lid closing off this container part, wherein the second coupling part is arranged on the cover. The coupling parts form a joint, thus serving as connection means that fasten the milk collection container to the breast shield.

In one example embodiment these coupling parts also serve as a milk line. For this purpose a connection channel between the breast shield and the milk collection container is provided in order to lead milk from the breast shield to the milk collection container, wherein this connection channel leads through the two coupling parts. In another example embodiment this connection channel extends, however, outside the two coupling parts.

In one example embodiment the two coupling parts form part of the milk collection container respectively of the breast shield. The first coupling part may be formed as a single piece that is part of the breast shield, and/or the second coupling part may be formed as a single piece that is part of the milk collection container. Overall, the breast shield can be designed so as to be in a single piece or it can comprise several parts.

In another example embodiment, at least one of the two coupling parts, and preferably both coupling parts, are a part that is additional to the milk collection container and the breast shield, wherein the additional coupling part in the direction of the connection between the milk collection container and the breast shield comprises a length that is significantly shorter than the height of the milk collection container and/or of the breast shield. Consequently the pumping unit as a whole continues to be compact and space-saving in its design. However, production of the individual parts is facilitated.

The relative movement between the milk collection container and the breast shield can take place on a single swivel axis. In one example embodiment, however, the relative movement is possible on several axes. For example, the relative movement may allow a swivel movement in three-dimensional space.

In one example embodiment, the relative movement is made possible by means of a joint between the milk collection container and the breast shield. The pumping unit can comprise a locking device for fixing the set angle. Preferably, however, the joint is designed so as to be self-locking.

In one example embodiment, the milk collection container is connected to the breast shield by way of a ball joint. In one example embodiment, the ball joint comprises a connection channel that connects an interior space of the breast shield to an interior space of the milk collection container in order to lead milk from the breast shield to the milk collection container. This connection is easy to establish and to disconnect and allows any pivoting angle in the three-dimensional space. Furthermore, it is advantageous that the ball joint, when disassembled, is easy to clean. It furthermore ensures a tight seal and in a simple manner makes it possible to arrange the connection channel in the joint itself.

In one example embodiment, the ball joint comprises a joint ball that is formed to or arranged on the breast shield. The ball joint further comprises a ball holder that is formed to or arranged on a lid of the milk collection container. The arrangement can also be the other way around. Thus, in another preferred embodiment the joint ball is formed to or arranged on a lid of the milk collection container.

In another example embodiment the joint is a hinge.

In yet another example embodiment the joint is a flexible connection piece that connects the milk collection container to the breast shield.

In one example embodiment, at a suitable position in the pumping unit a non-return valve is arranged. This non-return valve prevents milk from the collection container from being able to flow back into the breast shield. The term "suitable position" refers to a position that as far as possible minimizes the dead volume in the breast shield, thus keeping the space to be subjected to negative pressure during expressing as small as possible. The connection channel is a preferred position for the arrangement of the valve. The valve can be directly inserted, be formed in a single piece, or by means of a slide-in or insert element can be affixed in the unit, in particular in the channel. The valve may be a duckbill valve or a membrane valve. Other valve types can also be used.

The breast shield according to the invention for use in a pumping unit as described above comprises a coupling part that allows relative movement between the breast shield and a milk collection container in a state in which the milk collection container is attached to the breast shield.

The milk collection container according to the invention for use in a pumping unit as described above is designed to be dimensionally stable or approximately dimensionally stable and comprises a coupling part that allows relative movement between the milk collection container and a breast shield in a state in which the milk collection container is attached to the breast shield.

The coupling unit according to the invention for use in a pumping unit as described above comprises a first coupling part and a second coupling part for connecting a breast shield with a dimensionally stable or approximately dimensionally stable milk collection container, wherein the first and the second coupling part together allow relative movement between the breast shield and the milk collection container attached to the breast shield.

BRIEF DESCRIPTION OF THE DRAWINGS

Below, preferred embodiments of the invention are described with reference to the drawings that are merely used for clarification and are not to be interpreted as being limiting. The drawings show the following.

DETAILED DESCRIPTION

Figure 1:
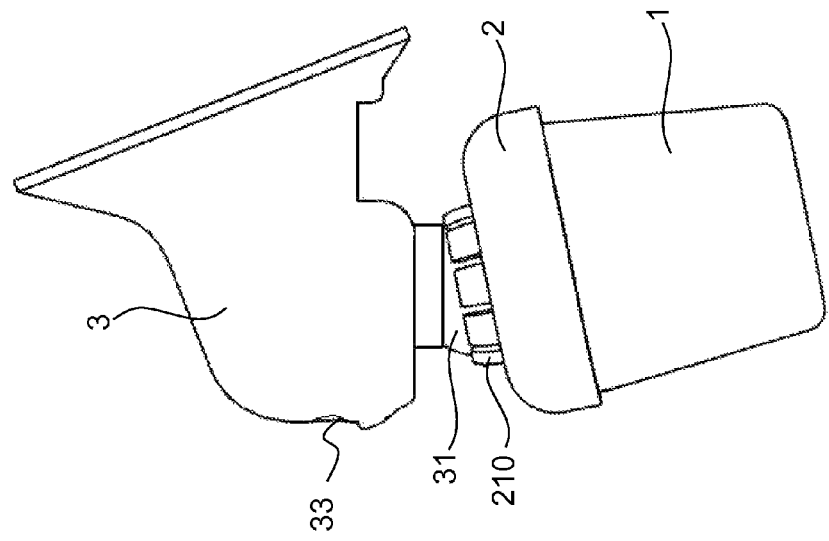
FIG. 1 shows a lateral view of a pumping unit according to the invention according to a first exemplary embodiment in a first position.
Figure 2:
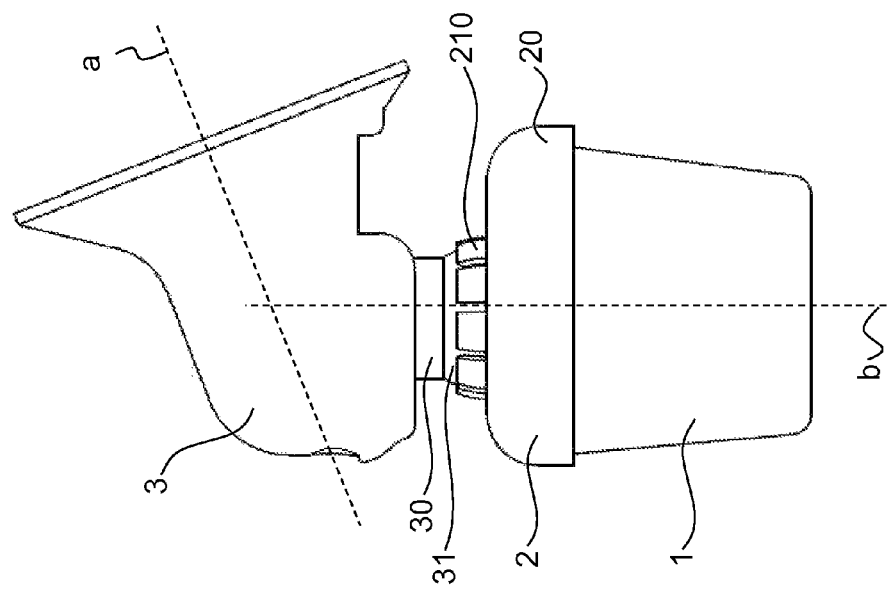
FIG. 2 shows the pumping unit according to FIG. 1 in a second position.
Figure 3:
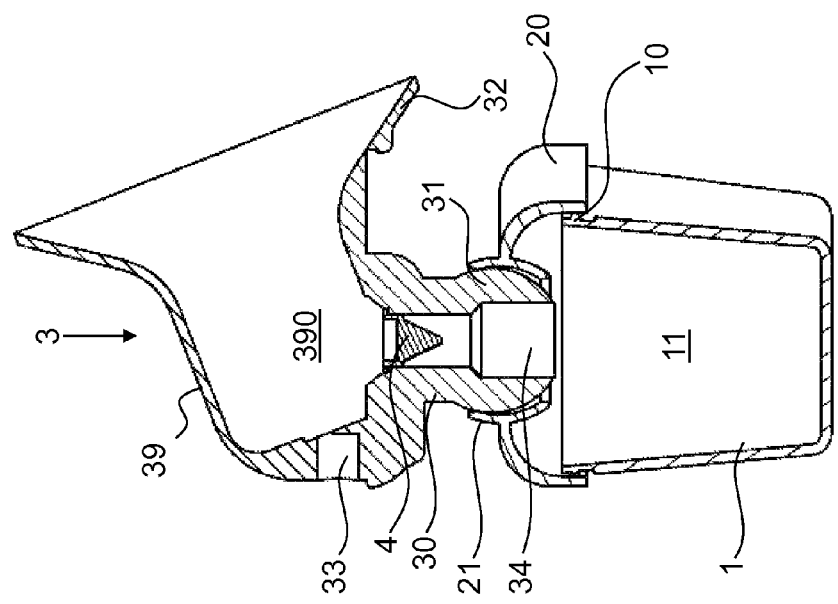
FIG. 3 shows a longitudinal section of the pumping unit according to FIG. 1.

FIGS. 1 to 3 show a first exemplary embodiment of the pumping unit according to the invention. Said pumping unit comprises a milk collection container including a container part 1 and a lid 2, and a breast shield 3. The breast shield 3 comprises a first longitudinal centre axis a, and the milk collection container comprises a second longitudinal centre axis b. These axes a, b are arranged at an angle to each other.

The milk collection container comprises the container part 1 with an interior space for receiving the expressed milk, and a lid 2 that closes off this container part 1. At least the container part 1, and preferably also the lid 2, is/are designed so as to be dimensionally stable or approximately dimensionally stable. Preferably, they are designed so as to be relatively rigid. Usually they comprise a plastic material. In a simple embodiment the lid 2 can be removably put onto the container part 1. For this purpose the container part 1 comprises one or several retention ribs 10 that are arranged circumferentially at its upper circumference and that engage the lid 2, preferably by way of a corresponding circumferential groove. If the container is round, as an alternative a rotary closure can also be used. Clamps or other attachment means are also possible.

In one example embodiment, the container part 1 comprises a self-standing design. To this effect it comprises a stable bottom region or protruding base studs.

The lid 2 comprises a cover body 20 with an upwards-facing surface. This surface comprises a joint ball mounting 21. The joint ball mounting 21 is designed so as to be partly spherical in shape, wherein resilient clamps 210 encompass a round opening. This round opening leads to the interior of the container part 1.

The breast shield 3 may be made of plastic. The breast shield 3 comprises an outward-expanding funnel 32 for receiving the mother's breast. The funnel 32 ends in a tubular section 39 with a vacuum connection 33 for connection to a vacuum pump; respectively, to a hose leading to a vacuum pump. The funnel 32 and the tubular section 39 are both kept so as to be relatively small. Instead of the classical funnel shape shown, other shapes of breast shields can also be used. This also applies to the remaining exemplary embodiments described in this text. The breast shield 3 may be formed in one piece, as shown in FIG. 1. However, the breast shield 3 can also be formed in several pieces. The breast shield 3 is preferably made from a rigid or approximately rigid material. The breast shield 3 can, however, in particular in the region of the funnel 32, also comprise a relatively soft material that conforms to the shape of the mother's breast. At least the tubular part 39 is, however, preferably designed so as to be rigid or at least dimensionally stable. These variants, too, are possible for the remaining exemplary embodiments.

The lower region of the tubular section 39 of the breast shield 3 makes a transition to a stiff neck 30, which comprises a joint ball 31. The joint ball 31 is detachably held in the joint ball mounting 21. The joint ball 31 can be rotated within the holder, wherein the joint is preferably designed so as to be self-locking so that without any further fixing means the joint ball 31 and thus the breast shield 3 remain in a position, selected by the mother, relative to the container. Such self-locking preferably takes place by means of the resilient clamps 210.

A connection channel 34 extends through the neck 30 and the joint ball 31 and connects the interior space 390 of the breast shield 3 to the interior space 11 of the container part 1. In the connection channel 34 a non-return valve, in the present embodiment a duckbill valve 4, is arranged. In this exemplary embodiment the non-return valve rests against a step of the connection channel 34. This step is located at the upper end of the connection channel 34, i.e. at the transition to the tubular section 39. Consequently the valve 4 can be inserted to this position by way of the funnel 32 of the breast shield 3.

Figure 4:
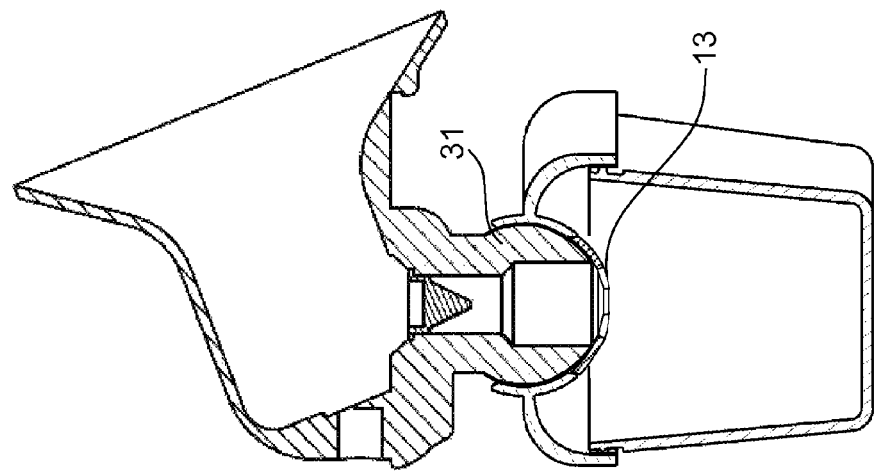
FIG. 4 shows a longitudinal section of an expanded embodiment of the pumping unit according to the invention according to FIG. 1.
Figure 6:
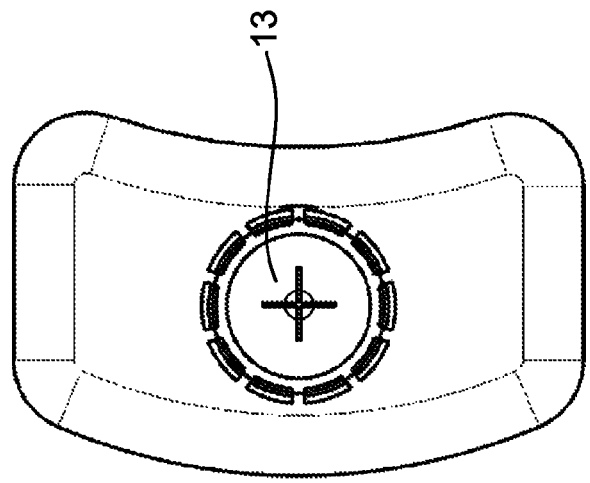
FIG. 6 shows a top view of the lid according to FIG. 4.
Figure 5:
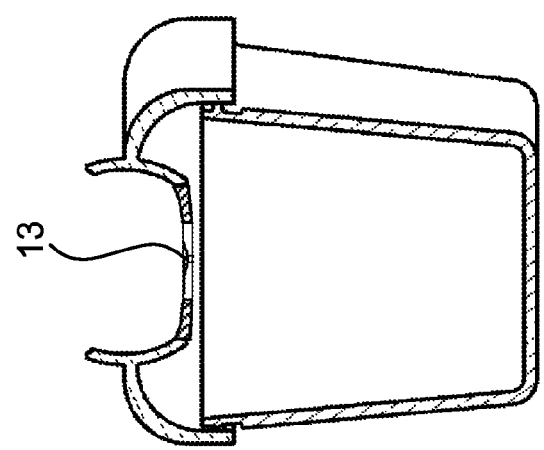
FIG. 5 shows a longitudinal section of the container part with lid according to FIG. 4.

FIGS. 4 to 6 show an expanded embodiment of the exemplary embodiment described above. In this embodiment the lid body 2 comprises a reversible closure device 13. This closure device 13 opens when the joint ball 31 is inserted. The closure device 13 can be designed as resilient segments, for example as shown in the diagram as a cross-slit diaphragm. Thus for storage purposes the container can be kept so as to be at least almost tight without there being a need for an additional lid.

Figure 7:
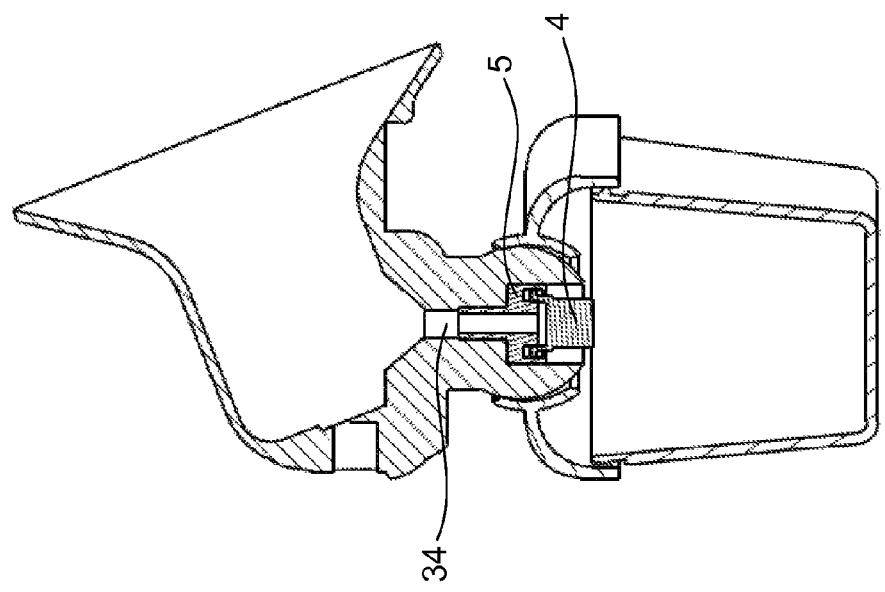
FIG. 7 shows a longitudinal section of a pumping unit according to the invention in a second embodiment.

In the embodiment according to FIG. 7 the valve 4 is kept in an insert element 5 that can be inserted from below, i.e. from the other free end of the connection channel 34. The channel 34 correspondingly comprises an end stop against which a circumferential shoulder of the insert element 5 rests.

The insert element 5 may also made from a plastic material. The valve 4 can be designed as a separate part, as shown here, or it can be made in one piece with the insert element 5.

Figure 8:
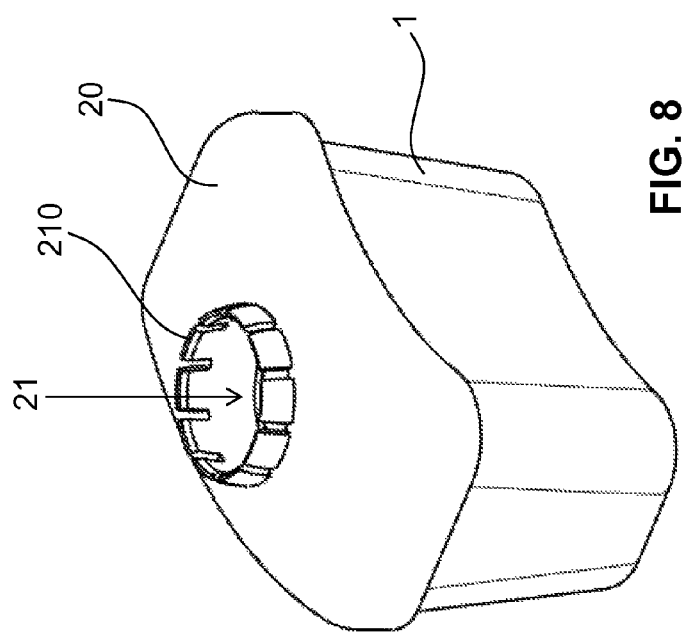
FIG. 8 shows a perspective view of a milk collection container for use in the pumping unit according to FIG. 1.

FIG. 8 shows a preferred shape of a milk collection container 1, 2 that can be used in the pumping unit according to the invention. The container part 1 may comprise a kidney-shaped cross-section so that it comprises an inwards-curved wall and an opposite, outwards-curved, wall. The lid may be designed analogously. The inwards-curved wall can be placed against the mother's body, e.g. against the mother's breast, so that the container can be brought very close to the body. This container can be used in all the embodiments described in this document of the pumping unit according to the invention. It can also be used in other pumping units in order to make possible as space-saving an arrangement on the breast as possible. Furthermore, it is advantageous if several container parts 1 can both be stacked in the vertical direction and placed beside each other without spaces in the horizontal direction. In this way they can be stored in an extremely space-saving manner.

Figure 9:
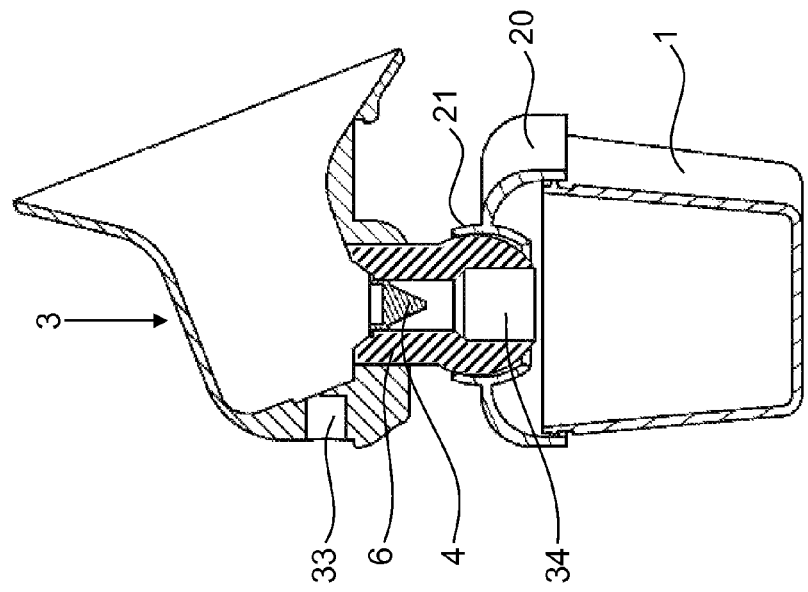
FIG. 9 shows a longitudinal section of a pumping unit according to the invention in a third embodiment.

In the embodiment according to FIG. 9 an adapter part 6 is arranged between the breast shield 3 and the milk collection container. The breast shield 3 is plugged onto the adapter part 6. Said breast shield 3 can be detachably connected to the adapter part 6 so that the individual parts can be cleaned and reassembled separately from each other. The breast shield 3 can, however, also be rigidly connected to the adapter part 6 so that it is not possible for separation in a non-destructive manner. This is advantageous in particular in the case of breast shields 3 intended for single use or for short-term multiple use.

The adapter part 6 forms the neck of the breast shield 3, and at its free end comprises the joint ball. A through-opening forms the connection channel 34. This embodiment, too, preferably comprises a non-return valve 4. The non-return valve 4 is again arranged at the upper end. However, the non-return valve 4 can also comprise the insert element 5 according to FIG. 7 or another valve arrangement.

Figure 11:
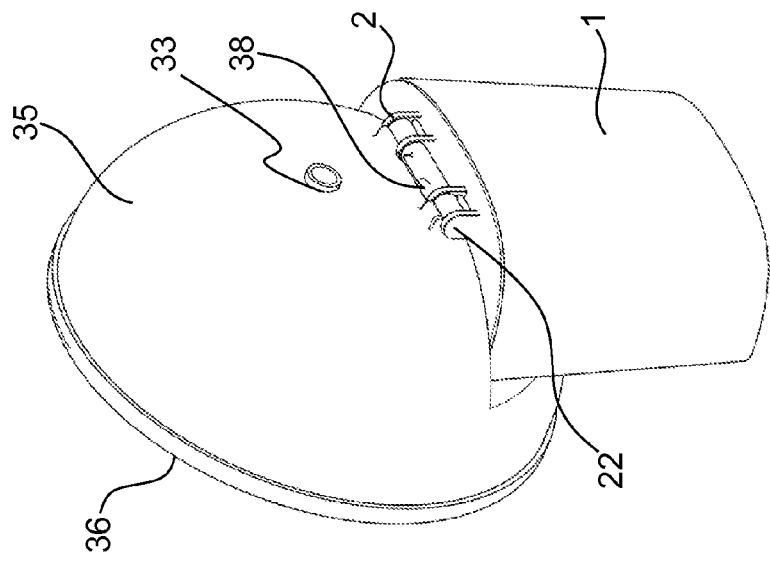
FIG. 11 shows a perspective view of the pumping unit according to FIG. 10 in a first position.
Figure 10:
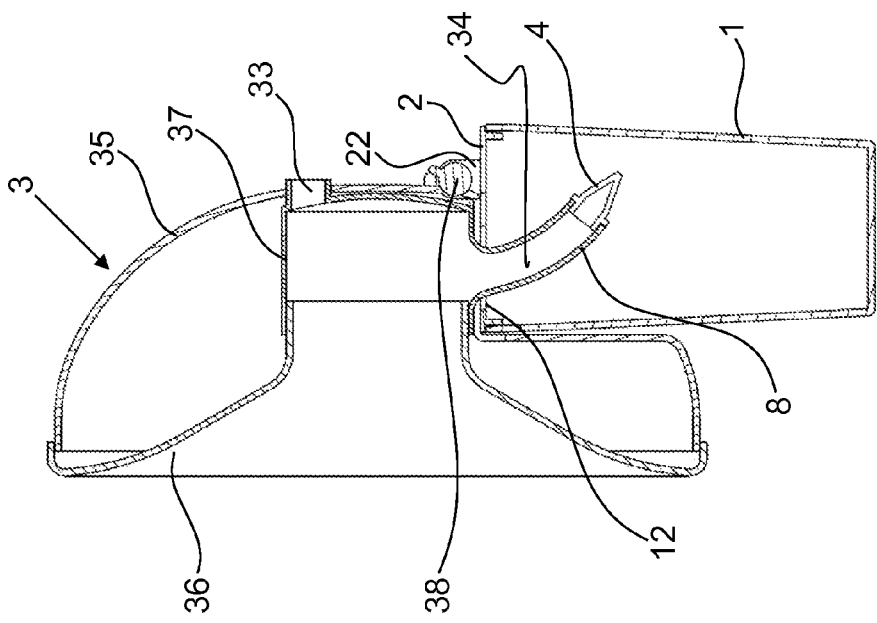
FIG. 10 shows a longitudinal section of a pumping unit according to the invention in a fourth embodiment.
Figure 13:
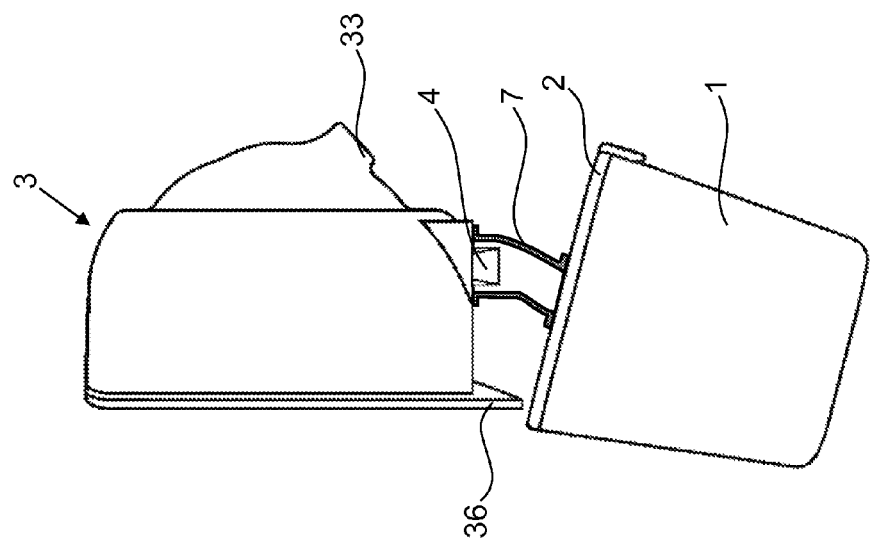
FIG. 13 shows a lateral view of a pumping unit according to the invention in a fifth embodiment in a first position.
Figure 12:
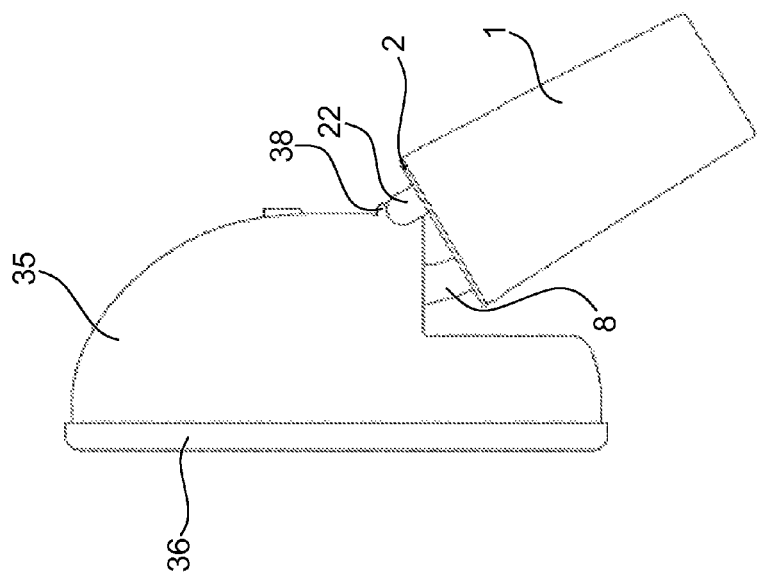
FIG. 12 shows a lateral view of the pumping unit according to FIG. 10 in a second position.

FIGS. 10 to 12 show a further exemplary embodiment. In the examples shown so far the milk was conveyed through the joint. In this example the joint is arranged so as to be separate from the connection channel 34. The joint is formed by a hinge joint. At the breast shield 3 a hinge pin 38 is attached, preferably formed in a single piece, and is pivotally held in a hinge bracket 22. The hinge bracket 22 in turn is attached to the lid 2 of the milk collection container, and may also be made in one piece with said lid 2. As shown in this example, the lid 2 is planar in shape. The lid 2 comprises a passage opening 12, spaced apart from the hinge, through which passage opening 12 a milk line 8 projects. The milk line 8 is firmly connected to the breast shield 3, thus forming the through-channel 34. The milk line 8 is preferably a rigid or flexible hose. Here again, a non-return valve 4 may be provided. The non-return valve 4 can, for example, be attached to the milk line 8 at the beginning or, as shown in the diagram, at the end of the milk line 8.

Additionally, in this example embodiment, an identical or similar breast shield 3 to that in the first example described with reference to FIGS. 1-6 can be used. However, the variant shown in this combination is space-saving and compact. It comprises a semi-circular, preferably rigid, breast shield shell 35 in which a funnel insert 36 is kept. It comprises a circumferential rim that has been put over the circumferential rim of the breast shield shell 35. The narrow end of the funnel insert 36 is held in a preferably rigid funnel mounting 37. The funnel mounting 37 is attached to the breast shield shell 35 and comprises a connection piece that penetrates the breast shield shell 35 towards the outside and forms the vacuum connection 33. In one example embodiment, as shown in FIG. 10, the milk line 8 is designed in a single piece with the funnel mounting 37. In another example embodiment, the milk line 8 may be attached to the funnel mounting 37.

As shown when considering FIGS. 10 and 12 together, the breast shield 3 can now be pivoted on a pivoting axis relative to the container. In this arrangement the passage opening 12 is sufficiently large for the milk line 8 to have enough play in it in order to take part in the movement without being kinked. It is not necessary for the container to be fully closed in this region.

Figure 16:
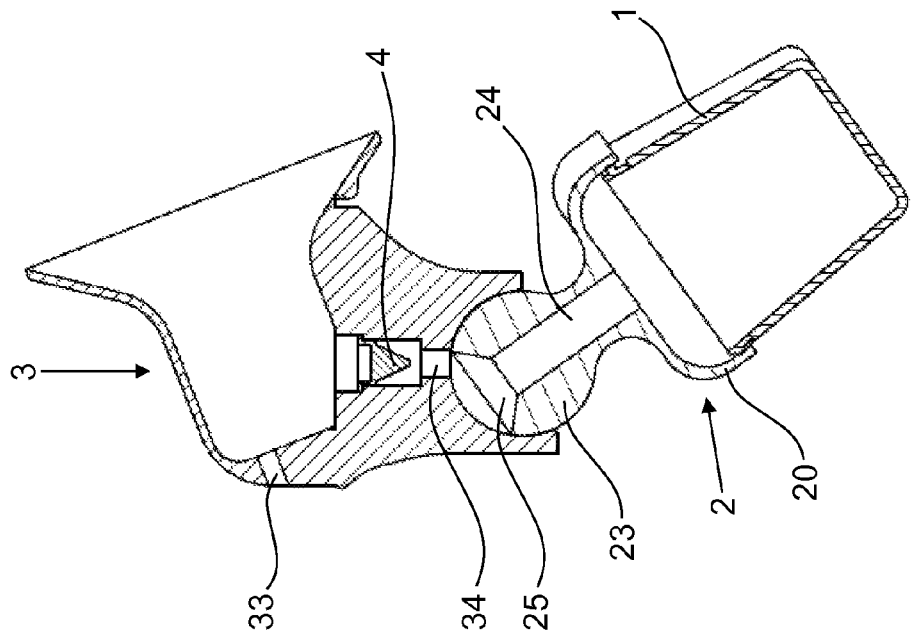
FIG. 16 shows a longitudinal section of a pumping unit according to the invention in a sixth embodiment.
Figure 14:
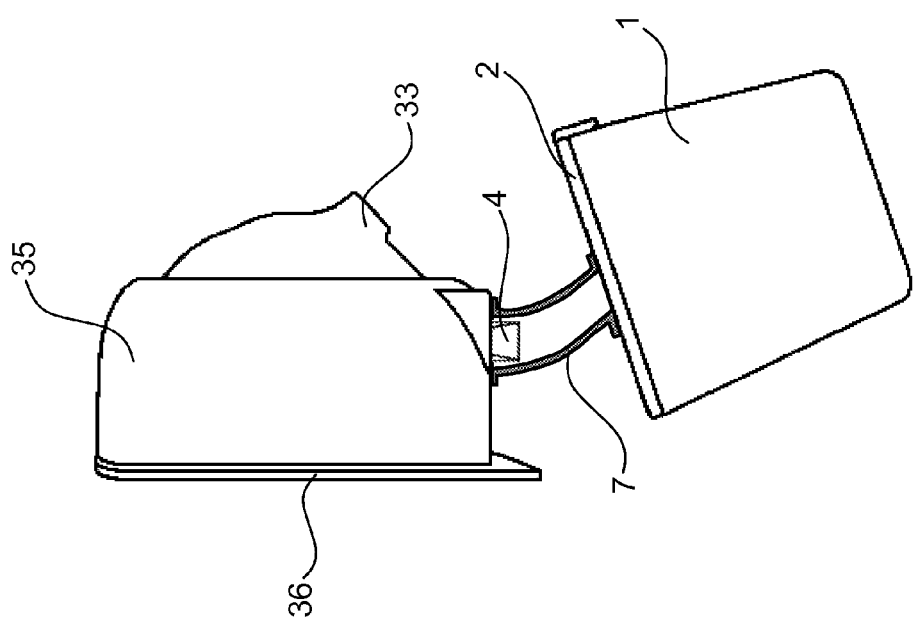
FIG. 14 shows a lateral view of the pumping unit according to FIG. 13 in a second position.

FIGS. 14 and 16 show a further embodiment. In this embodiment the joint is formed by a flexible connection piece 7. The length of the connection piece 7 preferably ranges from about 20 to 50 mm. The connection piece may be formed by a hose, preferably by a wide-ribbon hose, i.e. by a flat hose. In one example embodiment, said hose comprises structures on the inside, for example longitudinal ribs, to prevent it from kinking and/or from closing in cross-section. The hose is preferably designed to be sufficiently rigid to automatically hold a set position so that the container can carry the breast shield 3 within a particular range of pivoting angles at different pivoting angles and without external exertion of force.

Figure 15:
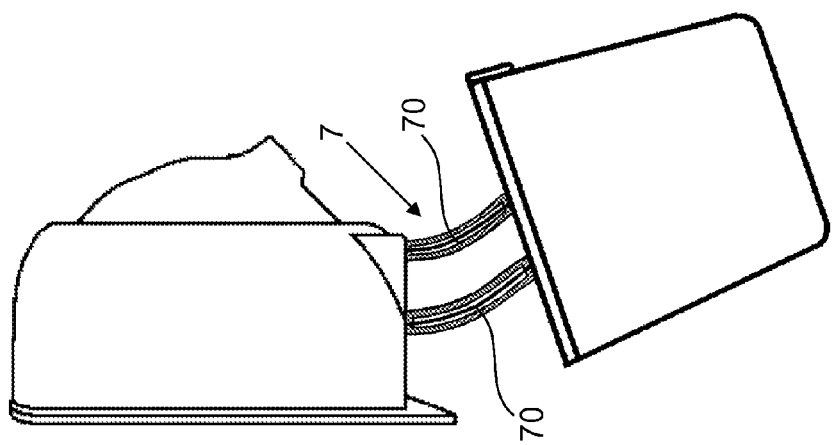
FIG. 15 shows a lateral view of a partial section of an expanded embodiment according to FIG. 13.

In one example embodiment shown in FIG. 15, the hose, respectively, the connection piece 7, comprises reinforcement elements. Preferably, the reinforcement elements are implemented by a wire 70 or by several wires 70 that are arranged in or on the wall of the connection piece 7.

The connection piece 7 is attached on the one hand to the breast shield 3 and on the other hand to the lid 2 of the milk collection container. The connection piece 7 can be attached so as to be detachable on both sides, or on one or both sides it can be firmly connected to said parts such that it cannot be detached without being destroyed. Preferably the connection piece 7 is inserted into and comprises corresponding retention ribs and/or retention grooves. The connection piece 7 preferably supports pivoting in a main direction at a slight inclination in other directions.

This exemplary embodiment may also comprise a non-return valve 4. In FIG. 15 the non-return valve 4 is again arranged in the breast shield 3.

In the embodiment according to FIG. 16 the joint is again a ball joint. However, in this embodiment a joint ball 23 is arranged on the lid 2 of the milk collection container and is in particular made in one piece with the lid 2. The breast shield 3 comprises a corresponding joint ball holder. The connection channel 34 of the breast shield 3 makes a transition to a connection channel 24 in the joint ball 23. To ensure that this connection remains open even at relatively large pivoting angles, the upper end of the connection channel 24 on the side of the cover 3 comprises a widening inlet funnel 25.

The pumping unit according to the invention can be designed in a compact and space-saving manner and is particularly suited to a hands-free arrangement.

The invention claimed is:

1. A pumping unit for use in a device for expressing human breast milk wherein the pumping unit comprises a breast shield for resting against a mother's breast and a dimensionally stable or approximately dimensionally stable milk collection container for receiving the expressed milk, wherein the breast shield comprises a first axis, and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the pumping unit comprises a first coupling part and a second coupling part, wherein the first coupling part and the second coupling part work together to enable the relative movement, wherein the first coupling part is arranged on the breast shield and the second coupling part is arranged on the milk collection container, wherein a connection channel between the breast shield and the milk collection container is provided to direct milk flow from the breast shield to the milk collection container, wherein the connection channel passes through the first and the second coupling parts and wherein there exists at least one position of the breast shield, where the connection channel extends in direction of the second axis.

2. The pumping unit according to claim 1, wherein the milk collection container comprises a container part and a lid closing off the container part, and wherein the second coupling part is arranged on the lid.

3. The pumping unit according to claim 1, wherein the first coupling part is formed in a single piece to a part of the breast shield and/or the second coupling part is formed in a single piece to a part of the milk collection container.

4. The pumping unit according to claim 1, wherein at least one of the two coupling parts is a part that is additional to the milk collection container and the breast shield, wherein the additional coupling part in the direction of the connection between the milk collection container and the breast shield comprises a length that is significantly shorter than the height of the milk collection container and of the breast shield.

5. The pumping unit according to claim 1, wherein the milk collection container is connected to the breast shield by way of a ball joint.

6. The pumping unit according to claim 5, wherein the ball joint comprises a the connection channel that connects the interior space of the breast shield to the interior space of the milk collection container in order to direct milk flow from the breast shield to the milk collection container.

7. The pumping unit according to claim 5, wherein the ball joint comprises a joint ball that is formed to or arranged on the breast shield, and wherein the ball joint comprises a ball holder that is formed to or arranged on a lid of the milk collection container.

8. The pumping unit according to claim 5, wherein the ball joint comprises a joint ball that is formed to or arranged on a lid of the milk collection container.

9. A pumping unit for use in a device for expressing human breast milk wherein the pumping unit comprises a breast shield for resting against a mother's breast and a dimensionally stable or approximately dimensionally stable milk collection container for receiving the expressed milk, wherein the breast shield comprises a first axis, and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the milk collection container is movably connected to the breast shield by way of a hinge and wherein a milk line is connected to the breast shield, forming a through channel that connects an interior space of the breast shield to an interior space of the milk collection container and wherein the milk collection container comprises a lid with a passage opening, through which passage opening the milk line projects.

10. A pumping unit for use in a device for expressing human breast milk wherein the pumping unit comprises a breast shield for resting against a mother's breast and a dimensionally stable or approximately dimensionally stable milk collection container for receiving the expressed milk, wherein the breast shield comprises a first axis, and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the milk collection container is connected to the breast shield by way of a flexible connection piece and wherein reinforcement elements are implemented in or on a wall of the flexible connection piece.

11. The pumping unit according to claim 1, wherein the milk collection container comprises a kidney-shaped cross-section.

12. A breast shield for use in a pumping unit, wherein the pumping unit comprises the breast shield for resting against a mother's breast and a dimensionally stable or approximately dimensionally stable milk collection container for receiving the expressed milk, wherein the breast shield comprises a first axis, and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the pumping unit comprises a first coupling part and a second coupling part, wherein the first coupling part and the second coupling part work together to enable the relative movement, wherein the first coupling part is arranged on the breast shield and the second coupling part is arranged on the milk collection container, wherein a connection channel between the breast shield and the milk collection container is provided to direct milk flow from the breast shield to the milk collection container, wherein the connection channel passes through the first and the second coupling parts and wherein there exists at least one position of the breast shield, where the connection channel extends in direction of the second axis.

13. A milk collection container for use in a pumping unit, wherein the pumping unit comprises the breast shield for resting against a mother's breast and the milk collection container for receiving the expressed milk, wherein the breast shield comprises a first axis, and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the milk collection container is designed to be dimensionally stable or approximately dimensionally stable and wherein the pumping unit comprises a first coupling part and a second coupling part, wherein the first coupling part and the second coupling part work together to enable the relative movement, wherein the first coupling part is arranged on the breast shield and the second coupling part is arranged on the milk collection container, wherein a connection channel between the breast shield and the milk collection container is provided to direct milk flow from the breast shield to the milk collection container, wherein the connection channel passes through the first and the second coupling parts and wherein there exists at least one position of the breast shield, where the connection channel extends in direction of the second axis.

14. A coupling unit for use in a pumping unit, wherein the pumping unit comprises a breast shield for resting against a mother's breast and a milk collection container for receiving expressed milk, wherein the breast shield comprises a first axis and the milk collection container comprises a second axis, wherein the milk collection container is removably attachable to the breast shield, and wherein in the attached state of the milk collection container the first axis is arranged at an angle to the second axis, wherein in the attached state the milk collection container is movable relative to the breast shield, and consequently the angle between the first axis and the second axis is variable, wherein the pumping unit comprises a first coupling part and a second coupling part, wherein the pumping unit first coupling part and second coupling part work together to enable the relative movement, wherein the pumping unit first coupling part is arranged on the breast shield and the pumping unit second coupling part is arranged on the milk collection container, wherein a connection channel between the breast shield and the milk collection container is provided to direct milk flow from the breast shield to the milk collection container, wherein the connection channel passes through the pumping unit first and second coupling parts and wherein there exists at least one position of the breast shield where the connection channel extends in direction of the second axis.

15. A coupling unit for a breast pump kit comprising:
a first coupling part that is removably attachable to a breast shield; and
a second coupling part that is removably attachable to a collection container;
wherein the first coupling part and the second coupling part are pivotable in relation to each other and are configured to allow for fluid flow therethrough; wherein the first coupling part comprises a joint ball and the second coupling part comprises a ball holder, or vice versa.

* * * * *